United States Patent [19]

Chesney et al.

[11] Patent Number: 5,316,004
[45] Date of Patent: May 31, 1994

[54] METHOD FOR VASCULAR IMPEDANCE MEASUREMENT

[75] Inventors: Charles F. Chesney, Sunfish Lake; Stanley M. Finkelstein, St. Louis Park; Jay N. Cohn, Minneapolis, all of Minn.

[73] Assignee: Regents of the University of Minnesota, Minneapolis, Minn.

[21] Appl. No.: 38,357

[22] Filed: Mar. 26, 1993

Related U.S. Application Data

[63] Continuation of Ser. No. 635,278, Dec. 28, 1990, Pat. No. 5,211,177.

[51] Int. Cl.⁵ ............................................. A61B 5/021
[52] U.S. Cl. ................................. 128/672; 128/713; 128/691; 128/668; 364/413.03
[58] Field of Search ............... 128/672, 668, 691, 692, 128/713; 364/413.03, 413.02

[56] References Cited

U.S. PATENT DOCUMENTS 5,103,828 4/1992 Sramek ............................ 128/668

Primary Examiner—William E. Kamm
Assistant Examiner—Kennedy J. Schaetzle
Attorney, Agent, or Firm—Merchant, Gould, Smith, Edell, Welter & Schmidt

[57] ABSTRACT

A vascular impedance measurement instrument includes a transducer to obtain a digitized arterial blood pressure waveform. The digitized data is used to determine cardiac output, and to subsequently obtain measurements of impedance parameters using the modified Windkessel model of the arterial system. The instrument is used as an aid in diagnosing, treating and monitoring patients with cardiovascular disease.

9 Claims, 4 Drawing Sheets $C_1$ = PROXIMAL ARTERIAL COMPLIANCE (ml/mm Hg);

$C_2$ = DISTAL ARTERIAL COMPLIANCE (ml/mm Hg);

L = INERTENCE (mm Hg/ml/s(2));

$P_1$ = PROXIMAL ARTERIAL (AORTIC) PRESSURE (mm Hg);

$P_2$ = DISTAL ARTERIAL (BRACHIAL) PRESSURE (mm Hg); AND

R = PERIPHERAL RESISTANCE (DYNES s $cm^{-5}$ ).

METHOD FOR VASCULAR IMPEDANCE MEASUREMENT

This is a continuation of application Ser. No. 07/635,278, filed Dec. 28, 1990, now U.S. Pat. No. 5,211,177.

TECHNICAL FIELD OF THE INVENTION

The present invention pertains generally to the field of cardiovascular medicine, and more particularly, to an instrument for characterizing the status of the cardiovascular system using an electrical analog model thereof.

BACKGROUND OF THE INVENTION

The modified Windkessel electrical analog model of the arterial system is gaining increasing attention from the medical community as a clinically useful tool for characterizing the human vasculature for the purpose of diagnosing, treating and monitoring cardiovascular disease. A number of studies of the cardiovascular system using the modified Windkessel model have been conducted, and correlations between the model parameters and normal and disease states have been identified. For instance, U.S. patent application Ser. No. 07/250,315, entitled "Method for Diagnosing Hypertension," discloses a method for utilizing the parameter $C_2$ of the modified Windkessel model to diagnose, treat and monitor the vascular disease condition underlying hypertension.

The modified Windkessel model of the arterial system is shown in FIG. 1. In the model:

$C_1$ = proximal arterial compliance (ml/mm Hg);
$C_2$ = distal arterial compliance (ml/mm Hg);
L = inertence (mm Hg/ml/s$^2$);
$P_1$ = proximal arterial (aortic) pressure (mm Hg);
$P_2$ = distal arterial (brachial) pressure (mm Hg); and
R = peripheral resistance (dynes sec cm$^{-5}$).

While the usefulness of the Windkessel model parameters for the diagnosis, treatment and monitoring of cardiovascular disease has become more apparent, they remain relatively difficult to use on a routine basis for two reasons. The first is the need to obtain a cardiac output measurement in order to determine the parameters. Conventional procedures for determining cardiac output, such as thermodilution and dye dilution, are surgically invasive, requiring catheterization of the patient. Physicians, in general, are reluctant to employ such procedures because of their cost, the discomfort and inconvenience to the patient, the risk of infection and other severe complications, and their relative level of complexity as compared to alternative noninvasive procedures. The second reason involves the difficulty with obtaining patient data for the modified Windkessel model from blood pressure waveforms, which also conventionally requires the insertion of an arterial catheter and the use of a transducer and other electronic equipment.

The present invention, as described hereinafter, provides an instrument which can noninvasively measure Windkessel parameters, or other impedance parameters which depend on cardiac output measurement, using a noninvasively obtained arterial blood pressure waveform of the patient. Accordingly, it is contemplated that the present invention will significantly facilitate widespread clinical use of the modified Windkessel model parameters, or other impedance model parameters, in the diagnosis, treatment and monitoring of cardiovascular disease. In particular, the invention allows for a quick, easy-to-use and noninvasive determination of the modified Windkessel parameters so that these parameters can be ascertained and used during routine physical examinations, and patient screening, treatment and monitoring. Given that the only existing practical and quick screening device for determining the status of the cardiovascular state is a blood pressure cuff (i.e., a sphygmomanometer) measurement, it is contemplated that the invention could provide a substantial and new diagnostic capability for physicians to use on a routine basis.

SUMMARY OF THE INVENTION

The present invention provides a vascular impedance parameter measurement method wherein a transducer is used to convert a noninvasively obtained blood pressure waveform signal to a corresponding analog electrical signal, and that signal is digitized to produce a series of digitized data samples representing a waveform of the arterial blood pressure. The digitized heart beat signal is processed and a segment of the heart beat signal corresponding to diastole is as marked, to determine injection time by measuring the duration of the segment. The sample series is further processed to determine a mean arterial pressure of the patient. Further processing of the ejection time and other patient data is used to determine a cardiac output measurement value for the patient, and the sample series and the cardiac output value and mean arterial pressure are processed to determine for the patient one or more parameters of a vascular impedance model. The parameters are measures of vascular impedance properties. Finally, the method calls for display of the one or more parameters.

DETAILED DESCRIPTION OF THE INVENTION

Figure 2:
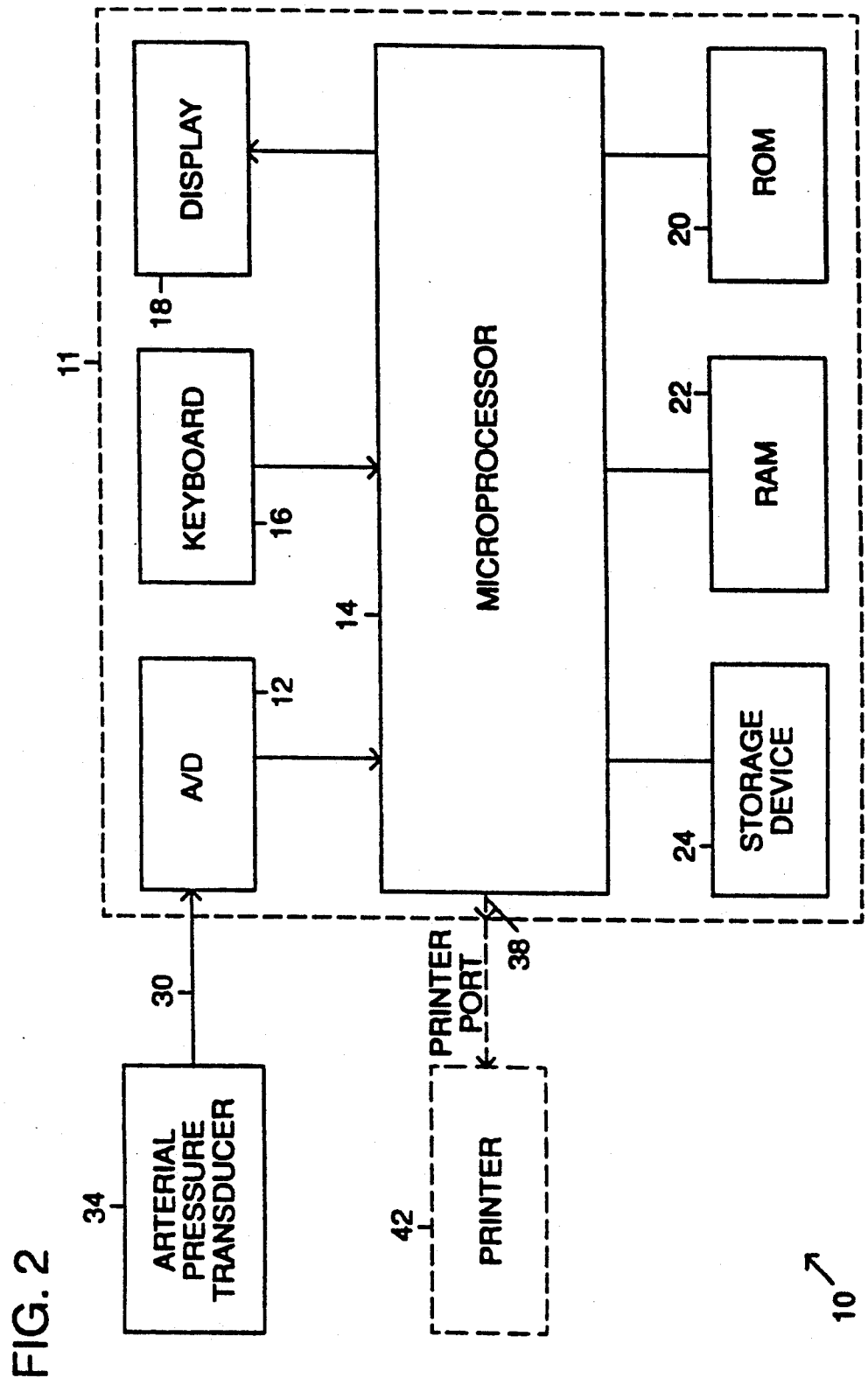
FIG. 2 is a schematic block diagram of the modified Windkessel parameter vascular impedance measurement instrument according to the present invention.

The modified Windkessel parameter vascular impedance measurement instrument 10 according to the present invention is shown in simplified schematic block diagram form in FIG. 2. The instrument 10 includes a transducer unit 34, a computer system 11, and optionally a printer 42. System 11 includes an analog to digital convertor (A/D) 12, preferably 12-bit, and a microprocessor unit 14, for instance a model 80386 by Intel, a keyboard input 16, a display 18, a ROM 20, a RAM 22 and a storage device 24. An input port 30 is provided to receive analog signal input from an arterial pressure transducer unit 34. Microprocessor 14 includes an output port 38 connected to optional printer 42.

Transducer unit 34 is preferably a noninvasive arterial blood pressure waveform measurement device, for example, a finger-cuff transducer unit using a counter pulsation technique wherein the waveform is detected by balancing the air pressure in a finger cuff with the blood pressure in the patient's finger. A commercially available finger-cuff transducer unit of this type is the Finapres® Continuous NIBP Monitor Model 2300, from Ohmeda Monitoring Systems division of the BOC Group, Inc., 355 Inverness Drive South, Englewood, Colo. 80112-5810. The Finapres® device produces an analog output signal which is fed through port 30 to A/D converter 12. Another noninvasive transducer unit available for use with the present invention is the Model 506 Non-Invasive Patient Monitor from Criticare Systems, Inc., 20900 Swenson Drive, Suite 398, Waukesha, Wis. 53186. A third commercially available transducer unit is the Model CMB-7000 from Nellcor Incorporated, 25495 Whitesell Street, Hayward, Calif. 94545. This unit noninvasively measures arterial blood pressure and provides waveform data based on the technique of arterial tonometry. It is also contemplated that the measured waveform may be transformed in digital form from the transducer unit 34 directly to the microprocessor 14, avoiding the need for A/D converter 12.

The arterial waveform may also be obtained invasively, if desired, although this is not believed to be preferred from a cost, medical risk and patient convenience perspective, using a Statham P23Db pressure transducer as unit 34. If obtained invasively, preferably, such a transducer would be connected to a patient's brachial artery via an 18-gauge, 2-inch Teflon catheter. This catheter-transducer system has an undamped natural frequency higher than 25 HZ and a damping coefficient less than 0.5, providing an acceptable frequency response. It shall be understood, however, that while the brachial artery is preferred, other peripheral arterial locations for obtaining the blood pressure waveforms can be substituted.

Figure 3:
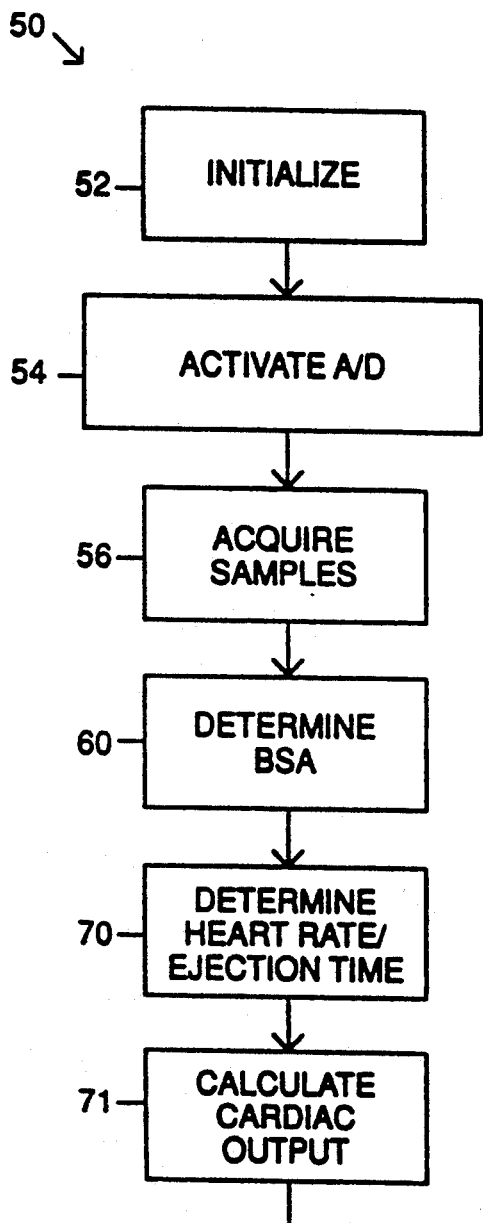
FIG. 3 is a schematic flow chart of the software components of the present invention.
Figure 3:
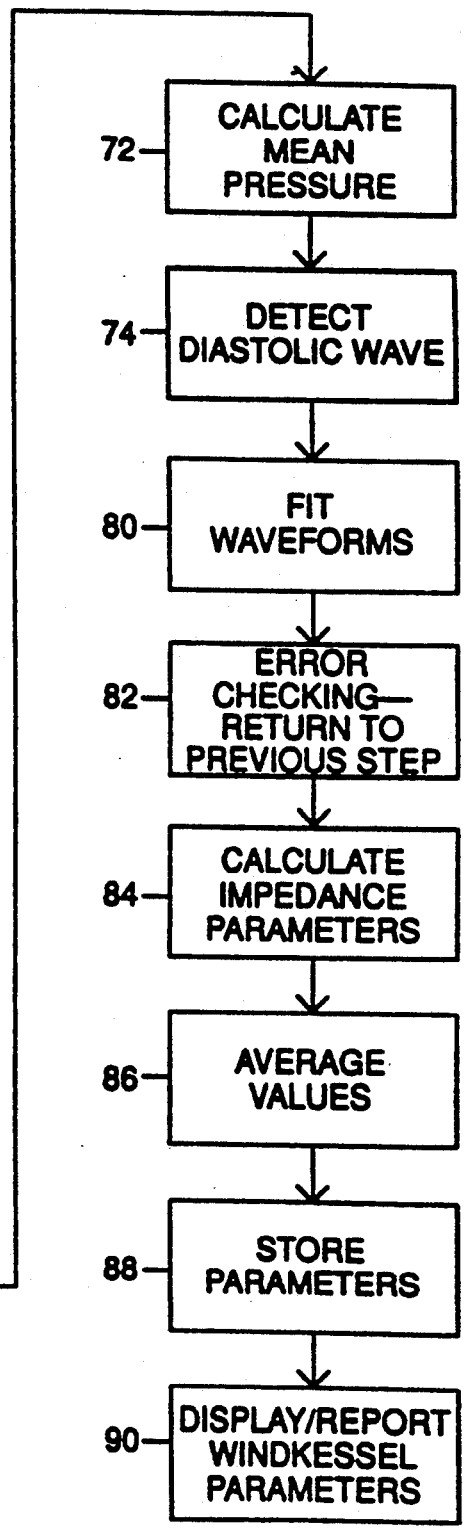

The software component 50 of the invention is illustrated in block diagram flow-chart form in FIG. 3. Software 50 is preferably stored in ROM 20 or storage device 24, and is referenced by microprocessor 14. Storage device 24 can be a hard disk, floppy disk or other digital storage system.

Figure 4:
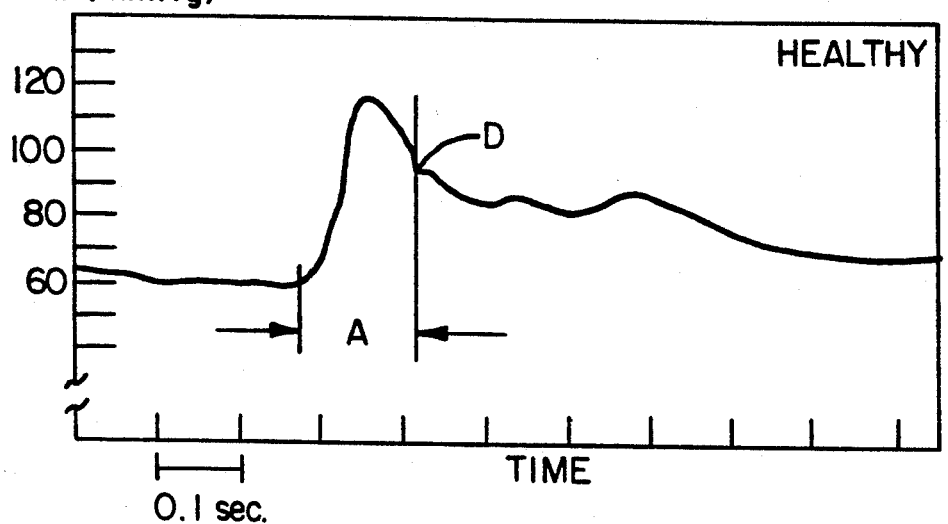
FIG. 4 is an illustrative example of a typical arterial blood pressure pulse contour or waveform in a healthy patient with the systolic ejection time marked as segment A.
Figure 5:
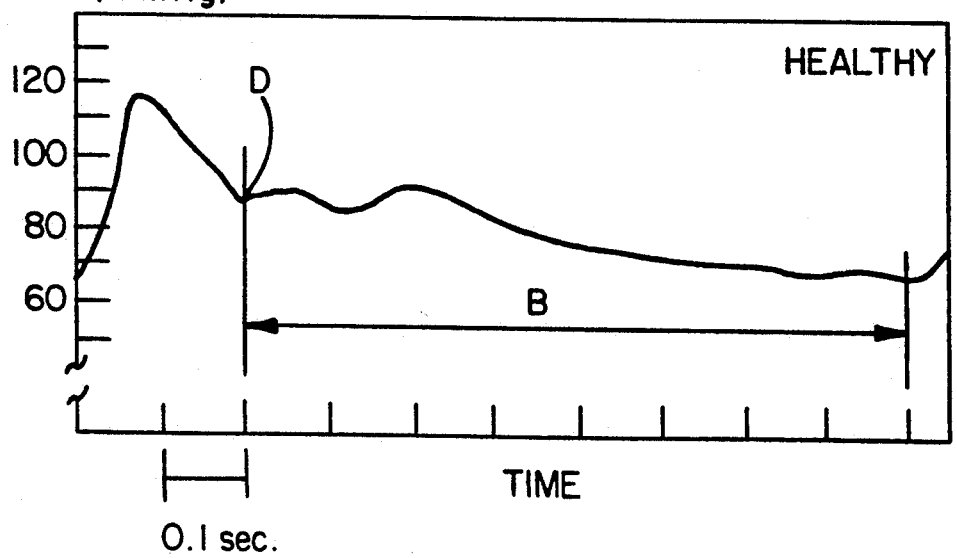
FIG. 5 is an illustrative example of typical arterial blood pressure pulse contour or waveform in a healthy patient with the diastolic decay time of the waveform marked as segment B.

Software 50 runs on microprocessor 14 to control the acquisition of arterial blood pressure waveform data, and to perform other instrument functions, as described below. An initialization and mode select routine 52 is provided for initializing microprocessor 14, including prompting the user to enter patient information, including the patient's age, height, weight, and/or body surface area. Routine 52 further provides that the waveform measurement process may be activated. If activated, A/D convertor 12 is activated (54) to digitize an analog blood pressure waveform signal generated by transducer 34. (Alternatively, as noted above, microprocessor 14 could obtain the pressure pulse measurements in digital form directly from transducer unit 34, if available, without the use of digitizer 54). FIGS. 4 and 5 illustrate typical arterial blood pressure waveforms for healthy patients.

The present invention uses an A/D sampling rate of 200 samples/second, which is satisfactory to capture the highest frequency components of interest in the arterial blood pressure waveform. It shall be understood, however, that higher or lower sampling rates may be used, and that the invention is in no way limited to the 200 samples/second rate. Routine 56 provides that the waveform data is sampled for approximately 30 seconds, producing in the range of 25 to 60 digitized arterial pulses, depending on the heart rate. The stream of digitized pulses are stored in RAM 22 or device 24 in the form of a continuous series of periodic time dependent data byte samples, with each data byte corresponding to the instantaneous pressure of the artery.

Routine 60 determines body surface area by standard formula, or alternatively, looks it up in a nomogram table stored in memory, using the patient's height and weight data. Alternatively, body surface area (BSA) can be determined by the physician or other care giver and entered directly into the instrument at routine 52, as noted above. A formula for determining BSA known to work in connection with the present invention is:

BSA $(m^{-2}) = 0.0072 \times weight^{0.425} \times height^{0.725}$ where weight is in kilograms and height is in centimeters.

A nomogram table known to work with the present invention is found in the Merck Manual, 12th edition, 1972 on page 1840 (reproduced from Wm. Brothby and R. B. Sandford, Boston Medical and Surgical Journal, Vol. 185, page 337, 1921).

Routine 70 performs three functions: (1) it selects consecutive heart beats; (2) determines the heart rate; and (3) determines the systolic ejection time of the heart.

First, routine 70 selects a group of consecutive representative beats (it has been found that six to ten beats are preferred, but the number used is in no way critical to the invention) preferably of comparatively low noise content. Representative beats are identified by establishing windows of permissible heart rate and mean arterial pressure values whereby abnormally fast or slow heartbeats, or high or low pressures can be rejected. The routine can thus pick the series of beats which is most representative.

Second, the heart rate (HR) is also determined by routine 70, by counting the number of beats per unit time. Where possible, it is preferable that the windows be tailored to the patient, thus allowing more precise selection of representative heart beats.

Thirdly, routine 70 determines systolic ejection time as follows. First, the arterial blood pressure waveforms are marked for analysis. When marked manually, a clinician can identify the onset of systole by the initial upstroke of arterial pressure. The end of systole, which is the onset of diastole, can be found manually by correlating to the second heart sound $S_2$, or by identifying the dicrotic notch on the arterial pressure wave. Ejection time is then determined by the time between the onset of systole and the beginning of diastole. For example, in FIG. 4, systolic ejection time is marked by segment A assuming a waveform obtained in the root of the aorta.

The present invention uses a software analysis algorithm at routine 70 to predict and select the segment A for each pressure waveform most probably corresponding to ejection time. Routine 70 searches the waveform data for the waveform upstroke marking systole, and then for the dicrotic notch (D), looked for after the peak of the systolic upstroke, and marks the onset of diastole just before the location of the dicrotic notch on the waveform. The ejection time (ET) is then determined from the location of the onset of systole and diastole. Transit time effects due to the distance between the proximal aorta and the arterial measurement site are taken into account in the ejection time measurement by moving back a predetermined interval (depending on where the arterial waveform is obtained in the arterial system) from the trough of the dicrotic notch to determine the end of systole for the purposes of the ejection time determination. The ejection time is thus the time between the upstroke (beginning of systole) and this point marking the end of systole. For waveforms obtained from the femoral or brachial artery, an interval of about 25 milliseconds has been found satisfactory to compensate for transit time effects. Shorter or longer intervals would be appropriate for waveforms obtained closer to or further from the heart, respectively.

Alternatively, instrument 10 can include means for digitizing an analog signal representing the heart sounds, software for identifying the first and second heart sounds $S_1$ and $S_2$, and for correlating them to the digitized arterial waveform to identify the onset of systole and diastole.

Routine 71 calculates stroke volume (SV) using the heart rate (HR), body surface area (BSA), ejection time (ET) and age for the subject, according to the following formula:

$SV = -6.6 + (0.25 \times ET) + (40.4 \times BSA) - (0.51 \times Age) - (0.62 \times HR)$, where SV equals stroke volume in ml/beat, ET is ejection time in msec, BSA is body surface area in square meters, Age is expressed in years, and HR is heart rate in beats per minute.

Once SV is known, cardiac output can be determined by multiplying heart rate (HR) times stroke volume (SV).

As illustrated in copending application Ser. No. 07/601,460, filed Oct. 23, 1990 and entitled "Method and Apparatus for Measuring Cardiac Output," hereby incorporated herein by reference, the cardiac output values obtained by the above-described system are relatively accurate. In approximately 90% of known cases the measurements have been within plus or minus 25% of the measurement obtained using a so-called "Gold Standard" thermodilution or dye dilution technique. This accuracy compares quite favorably against the 15-20% reproducibility of these dilution techniques.

It is currently contemplated that the formula for determining cardiac output set forth herein will be further refined and adjusted as additional data are collected and/or as adjustments to constants and factors are determined to produce more accurate determinations of cardiac output. The formula may be adjusted by performing a multiple linear regression to fit a new formula on "Gold Standard" data. Also, the particular formula set forth herein is not essential to the Windkessel parameter vascular impedance measurement instrument of the present invention. Other formulas and/or approaches to obtaining cardiac output measurements using the blood pressure waveform can be substituted for the particular formula set forth herein, provided that they give a reasonable degree of accuracy of measurement. References to other possible substitute approaches are given in the above-referenced application Ser. No. 07/601,460.

A routine 72 is provided to calculate the mean arterial pressure utilizing the blood pressure waveform data. The mean pressure value is used, as described herein, to determine the modified Windkessel parameters. With a cardiac output and mean arterial pressure value, the modified Windkessel parameters may be determined. To ascertain the modified Windkessel variables, the diastolic portion (i.e. that part of the pressure wave which corresponds to the period of diastole in the heart) of each selected beat must be identified and a routine 74 is provided for this purpose.

When marked manually, a clinician can identify the onset of diastole by correlating the second heart sound $S_2$ and the end of diastole by the upstroke of the following pulse. For example, in FIG. 5, diastole is marked by the segment B. However, for the sake of speed and simplicity, the present invention uses a software analysis algorithm to predict and select the segment in each pressure waveform most probably corresponding to diastole. Precise detection of onset is generally not critical because the slope of the pulse wave is generally uniform in the range of diastole onset. It is, however, important that the onset of the diastolic waveform to be used occur after the peak of systole and preferably within twenty milliseconds after the dicrotic notch (D). Thus, routine 74 searches the digital waveform representation for the dicrotic notch and marks the onset of diastole immediately thereafter on the waveform. The end of diastole in the waveform is easily located by finding the upstroke of the next pulse. With the relevant waveform segments so marked, the data for each pressure waveform can be analyzed to reveal the Windkessel vascular impedance properties of the patient.

Figure 1:
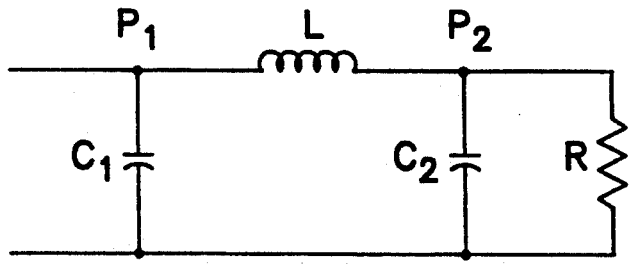
FIG. 1 is a circuit diagram of a modified Windkessel model of the vascular circulation.

The modified Windkessel model of the arterial system is used in the pulse contour analysis of the present invention. As shown in FIG. 1, the model includes components $P_1$, $P_2$, $C_1$, $C_2$, L and R in which:

$C_1$ = proximal compliance (ml/mm Hg)
$C_2$ = distal compliance (ml/mm Hg)
L = inertence (mm Hg/ml/s$^2$)
$P_1$ = proximal arterial pressure (mm Hg)
$P_2$ = brachial artery pressure (mm Hg)
R = peripheral resistance (dynes s cm$^{-5}$)

As taught, for example, by Goldwyn and Watt in I.E.E.E. Trans. Biomed. Eng. 1967; 14:11–17, the disclosure of which is hereby incorporated by reference herein, $P_2$ of the modified Windkessel model may be represented by the third order equation:

$$P_2(t) = A_1 \exp(-A_2 t) + A_3 \exp(-A_4 t) \cos(A_5 t + A_6),$$

wherein:

$$C_1 = \frac{mn - p}{mp} \cdot \frac{1}{R}$$

$$C_2 = \frac{1}{m} \cdot \frac{1}{R}$$

$$L = \frac{m^2 R}{mn - p} \text{ and}$$

wherein:
m = $A_2 + 2A_4$
n = $2 A_2 A_4 + A_4^2 + A_5^2$
and
p = $A_2(A_4^2 + A_5^2)$ Thus, knowing R, which can be calculated from cardiac output and mean arterial pressure as follows:

$$R = \frac{\text{mean arterial pressure}}{\text{cardiac output (milliliters/minute)}}$$

$C_1$, $C_2$ and L are readily calculated.

To accomplish the above, software 50 includes routine 80–82, which comprises a modified Gauss-Newton parameter-estimating algorithm as for the example referenced by Watt and Burrus in their paper entitled, "Arterial Pressure Contour Analysis for Estimating Human Vascular Properties," Journal of Applied Physiology, 1976; 40:171-176, the disclosure of which is hereby incorporated herein by reference. Routines 80-82 calculate the optimal values for coefficients $A_1$-$A_6$, using the measured arterial pressure data as $P_2(t)$. The algorithm uses an iterative approach which preferably provides fast convergence. The algorithm used in routines 80-82 include certain modifications. An automatic stopping procedure is included to stop iteration when an acceptable error level in the curve fitting threshold is reached or when convergence slows below a preset threshold. Also, when the process begins to diverge it returns to the previous best case. The routines also include a weighted iteration interval to improve convergence.

Once the coefficients $A_1$-$A_6$ are established for each pulse contour or waveform, the coefficients are used at routine 84 to calculate the $C_1$, $C_2$ and L vascular impedance parameters for each pulse contour or waveform. $C_1$, $C_2$ and L are all calculated in accordance with the formulas given above. Once calculated for each pulse contour the calculated values are averaged at routine 86, producing mean values more reliable for accuracy than any of the individual values. It shall be understood, however, that the averaging process is not essential. For instance, a median value could be selected for use if desired. At routine 88, the parameters may be stored in storage device 24 or RAM 22 for later retrieval. Finally, routine 90 causes the parameters $C_1$, $C_2$ and L to be displayed on display 18 and/or printed on printer 42.

Alternatively, routine 90 may additionally cause the display or report of cardiac output, mean arterial pressure, heart rate, and a tracing of the blood pressure waveforms.

Thus, the present invention provides an instrument which can noninvasively obtain measures of the modified Windkessel parameters. Accordingly, these parameters can be obtained quickly, inexpensively, easily and without discomfort to the patient, thereby encouraging more widespread beneficial use of the modified Windkessel model parameters in diagnosing, treating and monitoring patients with cardiovascular disease. Also, the vascular impedance measurement instrument provides a ready means to obtain modified Windkessel model parameters for subjects in clinical research trials and laboratory animals used in basic and applied biomedical research projects.

Although the invention has been described with respect to a second order modified Windkessel model of the vasculature, it is applicable to any model of the vasculature based on impedance which is derived from the blood pressure pulse contour of the arterial waveform and cardiac output. As an example, consider the first order model described by Spencer and Denison in "Pulsitile Blood Flow in the Vascular System. The Physiology of the Aorta and Major Arteries," in Hàmilton W. F., Dow P. Editors *Handbook of Physiology*, Section 2; circulation, Vol. 2. Washington, D.C. 1963 American Physiological Society, page 799. Spencer and Denison's RC model treats the arterial system as a simple first-order model which discharges during diastole into a single resistance (the vascular bed). In this model, $T = C \times R$, where T=reciprocal of the exponential slope discharge, C=capacitance, and R=resistance. Therefore, $C = T/R$.

A number of studies have been conducted using such a first order arterial model, including a number of studies by the French researchers A. Ch. Simon and M. E. Safar. Some of these studies have established normal and abnormal values for the first order parameters C and R, which thus can be used to determine if a patient falls within a normal range or not. Thus, as used in the claims appended hereto, the term "vascular impedance model," shall be inclusive of both the modified Windkessel model, the first order RC arterial model, and any other impedance model of an essentially equivalent nature.

Although the invention has been described herein in its preferred form, those of skill in the art will recognize that many modifications and changes may be made thereto without departing from the spirit and scope of the invention as set forth in the claims appended hereto.

What is claimed is:

1. A method for measuring vascular impedance properties from the blood pressure waveform of a patient, the waveform containing heart beat signals, comprising the steps of:

measuring and digitizing an arterial blood pressure of a patient to produce a series of digitized data samples representing a waveform of the arterial blood pressure of the patient;

processing a heart beat signal in the digitized blood pressure waveform, marking a segment of the heart beat signal corresponding to systole, and determining an ejection time by measuring the duration of said segment;

processing the same series to determine a mean arterial pressure of the patient;

processing said ejection time and other patient data to determine a cardiac output measurement value for the patient from at least said ejection time and other patient data; and processing the sample series and the cardiac output value and mean arterial pressure to determine for the patient one or more parameters of a vascular impedance model, the parameters being measures of vascular impedance properties.

2. A method for measuring vascular impedance properties from the blood pressure waveform of a patient, the waveform containing heart beat signals, comprising the steps of:

measuring and digitizing an arterial blood pressure of a patient to produce a series of digitized data samples representing a waveform of the arterial blood pressure of the patient, the waveform containing heart beat signals;

processing the heart beat signals in the digitized blood pressure waveform to select a group of representative heart beat signals, said heart beat signals selected according to predetermined criteria whereby unwanted signals are filtered out;

processing a heart beat signal in the digitized blood pressure waveform, marking a segment of the heart beat signal corresponding to systole, and determining an ejection time by measuring the duration of said segment;

processing at least said ejection time and other patient data to determine a cardiac output measurement value for the patient; and processing the sample series, the cardiac output value and mean arterial pressure to determine for the patient one or more parameters of a vascular impedance model, the parameters being measures of vascular impedance properties.

3. A noninvasive method for measuring vascular impedance properties from the blood pressure waveform of a patient, the waveform containing heart beat signals, comprising the steps of:
noninvasively measuring an arterial blood pressure of a patient using a technique of arterial tonometry and generating a corresponding analog arterial blood pressure waveform signal;
digitizing the blood pressure waveform signal to produce a corresponding series of digitized data samples representing the waveform of the arterial blood pressure of a patient; and
processing the sample series to determine a mean arterial pressure of the patient;
processing the sample series and other patient data to determine a cardiac output measurement value for the patient; and
processing the sample series and the cardiac output measurement value and mean arterial pressure to determine for the patient one or more parameters of a vascular impedance model, the parameters being measures of vascular impedance properties.

4. A method for measuring vascular impedance properties from the blood pressure waveform of a patient, the waveform containing heart beat signals, comprising the steps of:
measuring and digitizing an arterial blood pressure of a patient to produce a corresponding series of digitized data samples representing a waveform of the arterial blood pressure of the patient;
processing the sample series to determine a cardiac output measurement value for the patient;
processing heart beat signals in the digitized blood pressure waveform, and marking segments of the heart beat signals corresponding to diastole; and
processing the marked diastolic segments of the sample series and the cardiac output value and mean arterial pressure to determine for the patient one or more parameters of a vascular impedance model, the parameters being measures of vascular impedance properties.

5. The method according to claim 4 further wherein the step of processing the sample series determine a cardiac output measurement value includes the step of determining the measurement using the ejection time of the heart as determined from the sample series.

6. The method according to claim 5 further wherein the step of processing the sample series to determine a cardiac output value includes the step of determining stroke volume substantially in accordance with the following formula:

$$SV = -6.6 + (0.25 \times ET) + (40.4 \times BSA) - (0.51 \times Age) - (0.62 \times HR),$$

where SV equals stroke volume in ml/beat, ET is ejection time in msec, BSA is body surface area in square meters, Age is expressed in years, and HR is heart rate in beats per minute.

7. A method for processing the blood pressure waveform of a patient to determine the condition of a patient's vasculature from the shape of certain portions of the waveform, including at least the compliance of the patient's blood vessels, the waveform containing heart beat signals, comprising the steps of:
measuring and converting a blood pressure waveform of the patient to a corresponding analog signal;
digitizing the blood pressure waveform signal for a series of the patient's heart beats and storing the signal in a digital storage device;
processing the digitized blood pressure waveform signal to:
(a) count the number of heart beats per unit time in the digitized blood pressure waveform to produce a heart rate signal for the patient, and
(b) search a heart beat signal in the digitized blood pressure waveform, mark events indicating a beginning and ending of systole, and determine an ejection time signal by measuring a time between the marked events;
processing the heart rate signal, the ejection time signal, and values representing the patient's age and body surface area to generate an output signal indicative of the patient's cardiac output;
processing the digitized blood pressure waveform and determining therefrom a mean arterial pressure signal indicative of the patient's mean arterial pressure;
processing the digitized blood pressure waveform and marking segments of the waveform corresponding to a period of diastole in the heart; and
processing the marked segments of the digitized blood pressure waveform, the cardiac output signal and the mean arterial pressure signal, to analyze the shape of the marked diastolic segments and determine one or more signals representing a condition of the patient's vasculature from a vascular impedance model, the one or more signals including a least a compliance signal representative of the flexibility of the patient's blood vessels.

8. The method of claim 1, 2, 3, 4 or 7 further wherein the vascular impedance model is a modified Windkessel model of the vasculature.

9. The method of claim 1, 2, 3, 4 or 7 further wherein the vascular impedance model is a first order model of the vasculature.

* * * * *

UNITED STATES PATENT AND TRADEMARK OFFICE
CERTIFICATE OF CORRECTION

PATENT NO.: 5,316,004
DATED: May 31, 1994
INVENTOR(S): Chesney et al.

It is certified that errors appear in the above-identified patent and that said Patent is hereby corrected as shown below:

Add the following under the title of the patent and before the heading "Technical Field of the Invention":

--This invention was made with government support awarded by the National Institutes of Health. The government has certain rights in the invention.--

Signed and Sealed this

Twenty-fourth Day of April, 2001

*Attest:*

NICHOLAS P. GODICI

*Attesting Officer*   Acting Director of the United States Patent and Trademark Office